(12) United States Patent
Ryan et al.

(10) Patent No.: US 9,726,624 B2
(45) Date of Patent: Aug. 8, 2017

(54) USING MULTIPLE SOURCES/DETECTORS FOR HIGH-THROUGHPUT X-RAY TOPOGRAPHY MEASUREMENT

(71) Applicant: Jordan Valley Semiconductors Ltd., Migdal HaEmek (IL)

(72) Inventors: Paul Anthony Ryan, Darlington (GB); John Leonard Wall, Durham (GB); Matthew Wormington, Littleton, CO (US)

(73) Assignee: BRUKER JV ISRAEL LTD., Migdal Haemek (IL)

( * ) Notice: Subject to any disclaimer, the term of this patent is extended or adjusted under 35 U.S.C. 154(b) by 0 days.

(21) Appl. No.: 14/735,168

(22) Filed: Jun. 10, 2015

(65) Prior Publication Data

US 2015/0369761 A1    Dec. 24, 2015

Related U.S. Application Data

(60) Provisional application No. 62/013,628, filed on Jun. 18, 2014.

(51) Int. Cl.
*G01N 23/205* (2006.01)
*G01N 23/20* (2006.01)

(52) U.S. Cl.
CPC ... *G01N 23/2055* (2013.01); *G01N 23/20025* (2013.01); *G01N 2223/6116* (2013.01); *G01N 2223/6462* (2013.01)

(58) Field of Classification Search
USPC .......................................................... 378/74
See application file for complete search history.

(56) References Cited

U.S. PATENT DOCUMENTS

| 2,805,342 A | 9/1957 | Lang |
| 3,716,712 A | 2/1973 | Piwczyk |

(Continued)

FOREIGN PATENT DOCUMENTS

| DE | 19624094 C1 | 6/1997 |
| JP | 3075548 A | 3/1991 |

(Continued)

OTHER PUBLICATIONS

He, B., "Two-dimensional X-ray Diffraction", pp. 356-359, Published by John Wiley & Sons, Inc., USA, 2009.

(Continued)

*Primary Examiner* — Phillip A Johnston
(74) *Attorney, Agent, or Firm* — D. Kligler IP Services Ltd.

(57) ABSTRACT

An apparatus for X-ray topography includes a source assembly, a detector assembly, a scanning assembly and a processor. The source assembly is configured to direct multiple X-ray beams so as to irradiate multiple respective regions on a sample, wherein the regions partially overlap one another along a first axis of the sample and are offset relative to one another along a second axis of the sample that is orthogonal to the first axis. The detector assembly is configured to detect the X-ray beams diffracted from the sample and to produce respective electrical signals in response to the detected X-ray beams. The scanning assembly is configured to move the sample relative to the source assembly and the detector assembly along the second axis. The processor is configured to identify defects in the sample by processing the electrical signals, which are produced by the detector assembly while the sample is moved.

14 Claims, 4 Drawing Sheets

(56) References Cited

U.S. PATENT DOCUMENTS

| | | |
|---|---|---|
| 3,792,269 A | 2/1974 | Grienauer |
| 3,982,127 A | 9/1976 | Hartmann et al. |
| 4,242,588 A | 12/1980 | Silk et al. |
| 4,351,063 A | 9/1982 | Dineen et al. |
| 4,446,568 A | 5/1984 | Williams et al. |
| 4,696,024 A | 9/1987 | Pesch |
| 4,725,963 A | 2/1988 | Taylor et al. |
| 4,847,882 A | 7/1989 | Knoth et al. |
| 4,928,294 A | 5/1990 | Beard et al. |
| 4,989,226 A | 1/1991 | Woodbury et al. |
| 5,151,588 A | 9/1992 | Kiri et al. |
| 5,340,988 A | 8/1994 | Kingsley et al. |
| 5,373,544 A | 12/1994 | Goebel |
| 5,375,156 A | 12/1994 | Kuo-Petravic et al. |
| 5,418,828 A | 5/1995 | Carpenter |
| 5,481,109 A | 1/1996 | Ninomiya et al. |
| 5,491,738 A | 2/1996 | Blake et al. |
| 5,530,732 A | 6/1996 | Takemi |
| 5,574,284 A | 11/1996 | Farr |
| 5,588,034 A | 12/1996 | Bowen et al. |
| 5,619,548 A | 4/1997 | Koppel |
| 5,740,226 A | 4/1998 | Komiya et al. |
| 5,754,620 A | 5/1998 | Hossain et al. |
| 5,850,425 A | 12/1998 | Wilkins |
| 5,900,645 A | 5/1999 | Yamada |
| 5,923,720 A | 7/1999 | Barton et al. |
| 5,943,434 A | 8/1999 | Schwarz |
| 5,949,847 A | 9/1999 | Terada et al. |
| 5,963,329 A | 10/1999 | Conrad et al. |
| 6,041,098 A | 3/2000 | Touryanski et al. |
| 6,062,084 A | 5/2000 | Chang et al. |
| 6,072,854 A | 6/2000 | Kikuchi et al. |
| 6,111,930 A * | 8/2000 | Schipper .......... G01N 23/20025 206/557 |
| 6,192,103 B1 | 2/2001 | Wormington et al. |
| 6,226,347 B1 | 5/2001 | Golenhofen |
| 6,226,349 B1 | 5/2001 | Schuster et al. |
| 6,317,483 B1 | 11/2001 | Chen |
| 6,320,655 B1 | 11/2001 | Matsushita et al. |
| 6,331,890 B1 | 12/2001 | Marumo et al. |
| 6,381,303 B1 | 4/2002 | Vu et al. |
| 6,389,102 B2 | 5/2002 | Mazor et al. |
| 6,453,006 B1 | 9/2002 | Koppel et al. |
| 6,459,763 B1 | 10/2002 | Koinuma et al. |
| 6,504,902 B2 | 1/2003 | Iwasaki et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,574,305 B2 | 6/2003 | Boer et al. |
| 6,625,250 B2 | 9/2003 | Houge |
| 6,639,968 B2 | 10/2003 | Yokhin et al. |
| 6,643,354 B2 | 11/2003 | Koppel et al. |
| 6,665,372 B2 | 12/2003 | Bahr et al. |
| 6,680,996 B2 | 1/2004 | Yokhin et al. |
| 6,711,232 B1 | 3/2004 | Janik |
| 6,718,008 B1 | 4/2004 | He et al. |
| 6,744,850 B2 | 6/2004 | Fanton et al. |
| 6,744,950 B2 | 6/2004 | Aleksoff |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,768,785 B2 | 7/2004 | Koppel et al. |
| 6,771,735 B2 | 8/2004 | Janik et al. |
| 6,782,076 B2 | 8/2004 | Bowen et al. |
| 6,807,251 B2 | 10/2004 | Okanda et al. |
| 6,810,105 B2 | 10/2004 | Nasser-Ghodsi et al. |
| 6,813,338 B2 | 11/2004 | Takata et al. |
| 6,879,051 B1 | 4/2005 | Singh et al. |
| 6,891,627 B1 * | 5/2005 | Levy .................... G01N 21/211 257/E21.53 |
| 6,895,075 B2 | 5/2005 | Yokhin et al. |
| 6,898,270 B2 | 5/2005 | Lange et al. |
| 6,937,694 B2 | 8/2005 | Yokoyama et al. |
| 6,947,520 B2 | 9/2005 | Yokhin et al. |
| 6,963,630 B2 | 11/2005 | Umezawa et al. |
| 6,970,532 B2 | 11/2005 | Hayashi et al. |
| 6,987,832 B2 | 1/2006 | Koppel et al. |
| 6,996,208 B2 | 2/2006 | Helming et al. |
| 6,999,557 B2 | 2/2006 | Yamaguchi et al. |
| 7,003,075 B2 | 2/2006 | Miyake et al. |
| 7,035,373 B2 | 4/2006 | Omote |
| 7,062,013 B2 | 6/2006 | Berman et al. |
| 7,068,753 B2 | 6/2006 | Berman et al. |
| 7,076,024 B2 | 7/2006 | Yokhin |
| 7,110,491 B2 | 9/2006 | Mazor et al. |
| 7,113,566 B1 | 9/2006 | Peled et al. |
| 7,116,754 B2 | 10/2006 | Lischka et al. |
| 7,120,227 B2 | 10/2006 | Ozawa et al. |
| 7,120,228 B2 | 10/2006 | Yokhin et al. |
| 7,158,608 B2 | 1/2007 | Kucharczyk |
| 7,213,686 B2 | 5/2007 | Kaufman |
| 7,231,016 B2 | 6/2007 | Berman et al. |
| 7,242,743 B2 | 7/2007 | Fewster |
| 7,242,745 B2 | 7/2007 | He et al. |
| 7,258,485 B2 | 8/2007 | Nakano et al. |
| 7,280,200 B2 | 10/2007 | Plemmons et al. |
| 7,406,153 B2 | 7/2008 | Berman |
| 7,474,732 B2 | 1/2009 | Berman et al. |
| 7,483,513 B2 | 1/2009 | Mazor et al. |
| 7,508,504 B2 | 3/2009 | Jin et al. |
| 7,551,719 B2 | 6/2009 | Yokhin et al. |
| 7,629,798 B2 | 12/2009 | Mallory et al. |
| 7,742,564 B2 | 6/2010 | Parham et al. |
| 8,243,878 B2 | 8/2012 | Yokhin et al. |
| 8,503,611 B2 | 8/2013 | Kikuchi |
| 8,781,070 B2 | 7/2014 | Wormington et al. |
| 2003/0123610 A1 | 7/2003 | Okanda et al. |
| 2003/0157559 A1 | 8/2003 | Omote et al. |
| 2005/0023491 A1 | 2/2005 | Young et al. |
| 2009/0116727 A1 | 5/2009 | Jin et al. |
| 2009/0196489 A1 | 8/2009 | Le |
| 2011/0188632 A1 * | 8/2011 | Harding ............... G01V 5/0016 378/86 |
| 2012/0014508 A1 | 1/2012 | Wormington et al. |
| 2012/0099705 A1 * | 4/2012 | Murakoshi .......... A61B 6/4291 378/85 |
| 2012/0140889 A1 | 6/2012 | Wall et al. |
| 2012/0177182 A1 * | 7/2012 | Olesinski ............. G01V 5/0025 378/87 |
| 2012/0281814 A1 | 11/2012 | Yokhin et al. |

FOREIGN PATENT DOCUMENTS

| | | |
|---|---|---|
| JP | 5188019 A | 7/1993 |
| JP | 666741 A | 3/1994 |
| JP | 6258260 A | 9/1994 |
| JP | 6273357 A | 9/1994 |
| JP | 7311163 A | 11/1995 |
| JP | 8-313458 A | 11/1996 |
| JP | 9210663 A | 8/1997 |
| JP | 9-229879 A | 9/1997 |
| JP | 10048398 A | 2/1998 |
| JP | 10160688 A | 6/1998 |
| JP | 10206354 A | 8/1998 |
| JP | 10318949 A | 12/1998 |
| JP | 1114562 A | 1/1999 |
| JP | 11014561 A | 1/1999 |
| JP | 11304728 A | 11/1999 |
| JP | 200088776 A | 3/2000 |
| JP | 2000266698 A | 9/2000 |
| JP | 2000292379 A | 10/2000 |
| JP | 2000314708 A | 11/2000 |
| JP | 200166398 A | 3/2001 |
| JP | 2001153822 A | 6/2001 |
| JP | 2003194741 A | 7/2003 |
| JP | 2003329619 A | 11/2003 |
| JP | 2004257914 A | 9/2004 |
| JP | 2005172830 A | 6/2005 |
| JP | 2005214712 A | 8/2005 |
| JP | 2005265841 A | 9/2005 |
| JP | 2005315742 A | 11/2005 |
| JP | 2005326261 A | 11/2005 |

(56) References Cited

FOREIGN PATENT DOCUMENTS

| | | |
|---|---|---|
| JP | 2006317249 A | 11/2006 |
| WO | 9813853 A1 | 4/1998 |
| WO | 2004013867 A2 | 2/2004 |

OTHER PUBLICATIONS

Bowen et al., "X-Ray metrology by Diffraction and Reflectivity," CP550, Characterization and Metrology for ULSI Technology: 2000 International Conference, pp. 570-579, American Institute of Physics, 2001.
Cohen et al., "Characterization of the silicon on insulator film in bonded wafers by high resolution x-ray diffraction", Applied Physics Letters, vol. 75, No. 6, pp. 787-789, Aug. 9, 1999.
Cohen et al., "High-Resolution X-Ray Diffraction for Characterization and Monitoring of Silicon-on-Insulator Fabrication Processes," Journal of Applied Physics, vol. 93, No. 1, pp. 245-250, Jan. 1, 2003.
Goorsky et al., "Grazing Incidence In-plane Diffraction Measurement of In-plane Mosaic with Microfocus X-ray Tubes", Crystal Research and Technology, vol. 37, No. 7, pp. 645-653, year 2002.
Hayashi et al., "Refracted X-Rays Propagating Near the Surface under Grazing Incidence Condition," Spectrochimica Acta, Part B 54, pp. 227-230, year 1999.
Hu et al., "Small angle x-ray scattering metrology for sidewall angle and cross section of nanometer scale line gratings," Journal of Applied Physics, vol. 96, No. 4, pp. 1983-1987, Aug. 15, 2004.
Guerault, H., "Specular reflectivity and off-specular scattering: Tools for roughness investigation", Instituut voor Kern-en Stralingsfysica, 15 pages, Dec. 15, 2000.
Jones et al., "3-Dimensional Lineshape Metrology Using Small Angle X-ray Scattering", AIP Conference Proceedings, vol. 683, pp. 434-438, Sep. 30, 2003.
Jones et al., "Sub-Nanometer Wavelength Metrology of Lithographically Prepared Structures: A Comparison of Neutron and X-Ray Scattering", Proceedings of SPIE—the International Society for Optical Engineering, pp. 4059-4061, Jun. 1, 2003.
Jones et al., "Small Angle X-ray Scattering for Ssub-100 nm Pattern Characterization," Applied Physics Letters, vol. 83, No. 19, pp. 4059-4061, Nov. 10, 2003.
Jordan Valley, "How to Measure SiGe on SOI on BedeMetrixTM Tools", Electronic Materials Conference 2008, USA, 10 pages, Jul. 21, 2008.
Kojima et al., "Structural Characterization of Thin Films by X-ray Reflectivity," Rigaku Journal, vol. 16, No. 2, pp. 31-41, year 1999.
Kozaczek et al., "X-ray Diffraction Metrology for 200mm Process Qualification and Stability Assessment," Advanced Metallization Conference, Canada, 6 pages, Oct. 8-11, 2001.
X-Ray Optical Systems, Inc., "Monolithic Polycapillary Lens Information", Albany, USA, 1 page, Dec. 29, 1998.
Wu et al., "Substepping and its Application to HST Imaging", Astronomical Data Analysis Software and Systems VII ASP Conference Series, vol. 145, pp. 82-85, year 1998.
Naudon et al., "New Apparatus for Grazing X-ray Reflectometry in the Angle-Resolved Dispersive Mode," Journal of Applied Crystallography, vol. 22, pp. 460-464, year 1989.
Neissendorfer et al., "The Energy-Dispersive Reflectometer/Diffractometer at BESSY-I", Measurement Science Technology, vol. 10, pp. 354-361, IOP Publishing Ltd., year 1999.
Parrill et al., "GISAXS—Glancing Incidence Small Angle X-ray Scattering," Journal de Physique IV, vol. 3, pp. 411-417, Dec. 1993.
Powell et al., "X-ray Diffraction and Reflectivity Characterization of SiGe Superlattice", Semiconductor Science Technology Journal, vol. 7, pp. 627-631, year 1992.
Di Fonzo et al., "Non-Destructive Determination of Local Strain with 100-Nanometre Spatial Resolution," Nature, vol. 403, pp. 638-640, Feb. 10, 2000.
Ulyanenkov, A., "Introduction to High Resolution X-Ray Diffraction," Workshop on X-ray characterization of thin layers, Uckley, 50 pages, May 21-23, 2003.
Authier, A., "Dynamical Theory of X-Ray Diffraction", International Union of Crystallography, Monographs on crystallography 11, revised edition, pp. 101-102, Oxford University Press 2005.
Wiener et al., "Characterization of Titanium Nitride Layers by Grazing-Emission X-Ray Fluorescence Spectrometry", Applied Surface Science, vol. 125, pp. 129-136, Elsevier Science BV 1998.
Woitok et al., "Towards Fast Reciprocal Space Mapping," JCPDS—International Centre for Diffraction Data, Advances in X-ray Analysis, vol. 48, pp. 165-169, year 2005.
Oxford Instruments Inc., Series 5000 Model XTF5011 X-Ray Tube Datasheet, Scotts Valley, USA, 2 pages, Jun. 28, 2000.
Photonic Science Ltd., "X-Ray FDI Camera", pp. 1-5, Apr. 28, 2011.
Pesek et al., "Lattice Misfit and Relative Tilt of Lattice Planes in Semiconductor Heterostructures", Semiconductor Science and Technology Journal, vol. 6, pp. 705-708, IOP Publishing Ltd 1991.
"Computer-Controlled X-ray Topographic Imaging System", Rigaku Journal, vol. 1, No. 1, pp. 23-24, year 1984.
Price et al., "X-ray focusing with Wolter microchannel plate optics", Nuclear Instruments and Methods in Physics Research Section A: Accelerators, Spectrometers, Detectors and Associated Equipment, vol. 490, Issues 1-2, pp. 276-289, Sep. 1, 2002.
Bowen et al., "High Resolution X-Ray Diffractometry and Topography", Taylor & Francis, 41 pages (chapter 8, pp. 181-219),1998.

\* cited by examiner

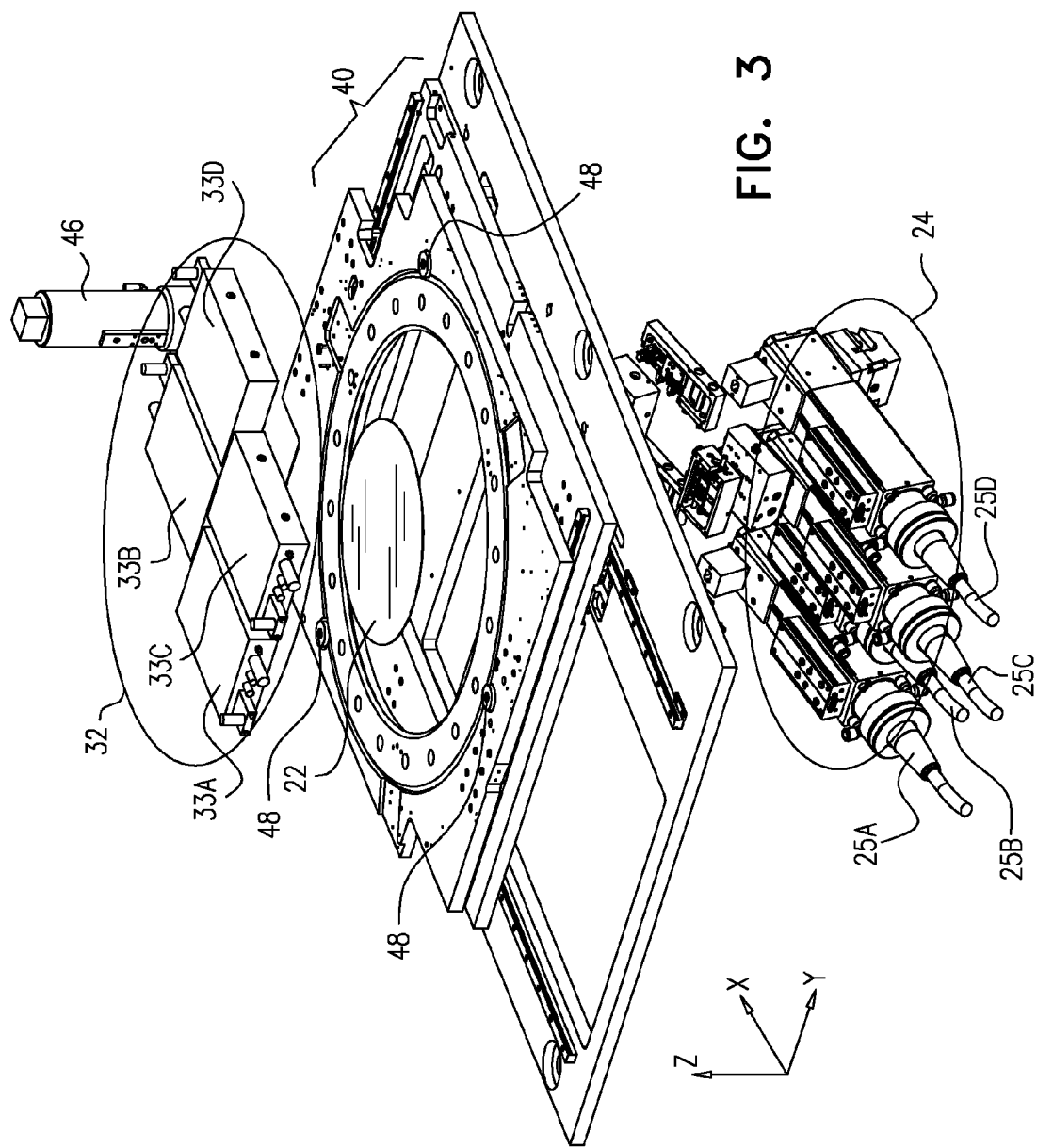

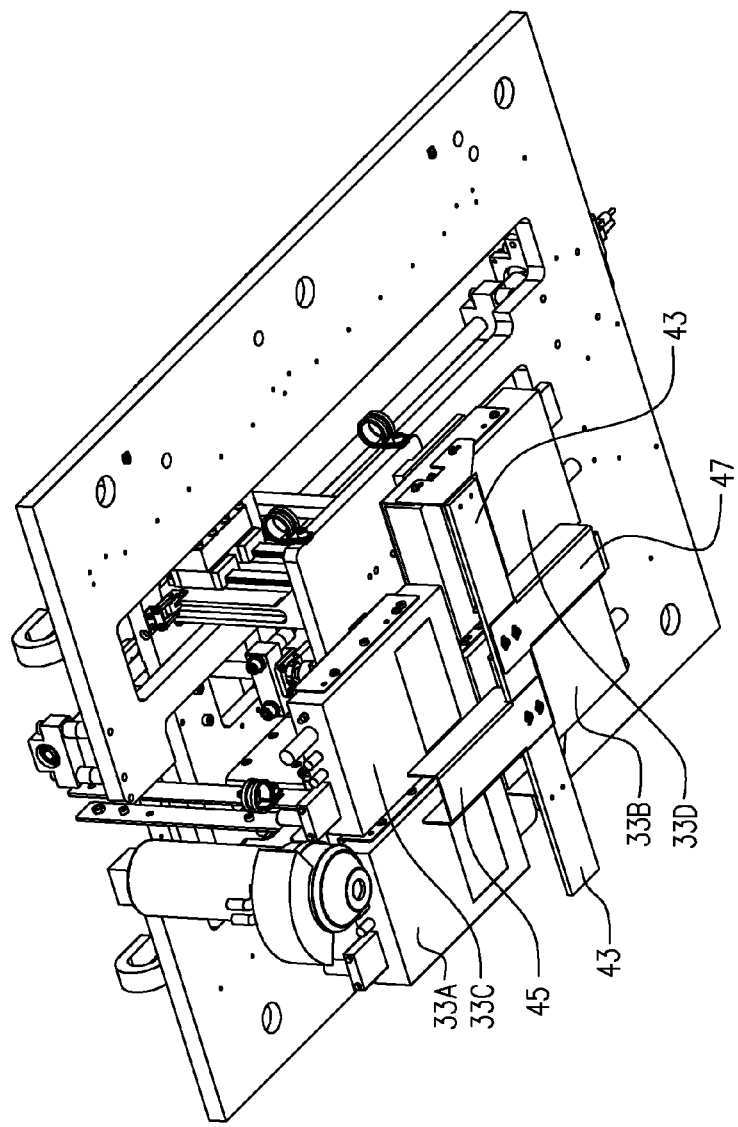
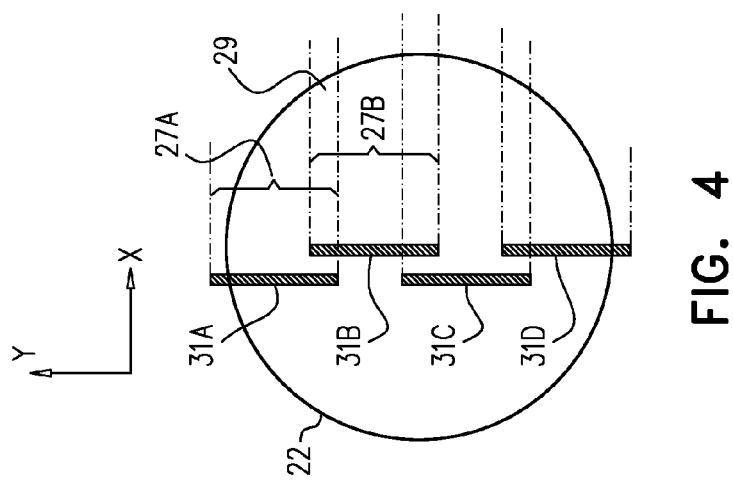
FIG. 5
FIG. 4

USING MULTIPLE SOURCES/DETECTORS FOR HIGH-THROUGHPUT X-RAY TOPOGRAPHY MEASUREMENT

CROSS-REFERENCE TO RELATED APPLICATIONS

This application claims the benefit of U.S. Provisional Patent Application 62/013,628, filed Jun. 18, 2014, whose disclosure is incorporated herein by reference.

FIELD OF THE INVENTION

The present invention relates generally to X-ray analysis, and particularly to methods and systems for X-ray analysis using multiple X-ray beams.

BACKGROUND OF THE INVENTION

Microelectronic samples, such as silicon wafers, may be damaged during shipping, handling or production. For example, mechanical damage may cause defects in the crystalline structure of the wafer. Various methods have been developed for detecting crystalline defects.

For example, U.S. Pat. No. 6,782,076, whose disclosure is incorporated herein by reference, describes an X-ray topographic system, comprising an X-ray generator producing a beam of X-rays impinging on a limited area of a sample such as a silicon wafer. A solid-state detector is positioned to intercept the diffracted beam after transmission through or reflection from the sample and produces a digital image of the area on which the X-rays impinge. Relative stepping motion between the sample and the X-ray generator produces a series of digital images, which are combined together. In optional embodiments, an X-ray optic is interposed to produce a parallel beam to avoid image doubling, or the effect of image doubling is removed by software.

U.S. Pat. No. 8,503,611, whose disclosure is incorporated herein by reference, describes an X-ray topography apparatus in which X-rays diffracted from a sample which is scanned with a linear X-ray, are detected by an X-ray detector to obtain a planar diffraction image. The X-ray detector is an imaging plate shaped as a cylinder and provided with a surface area that is larger than the sample, and the imaging plate is made to undergo $\alpha$-rotation about the center axis of the cylindrical shape in coordination with scanning movement of the linear X-rays. The center axis of the cylindrical shape extends in a direction at a right angle with respect to the direction of the scanning movement of the linear X-rays.

U.S. Pat. No. 8,781,070, whose disclosure is incorporated herein by reference, describes an apparatus for inspection of a disk, which includes a crystalline material and has first and second sides. The apparatus includes an X-ray source, which is configured to direct a beam of X-rays to impinge on an area of the first side of the disk. An X-ray detector is positioned to receive and form input images of the X-rays that are diffracted from the area of the first side of the disk in a reflective mode. A motion assembly is configured to rotate the disk relative to the X-ray source and detector so that the area scans over a circumferential path in proximity to an edge of the disk. A processor is configured to process the input images formed by the X-ray detector along the circumferential path so as to generate a composite output image indicative of defects along the edge of the disk.

SUMMARY OF THE INVENTION

An embodiment of the present invention that is described herein provides an apparatus for X-ray topography including a source assembly, a detector assembly, a scanning assembly and a processor. The source assembly is configured to direct multiple X-ray beams so as to irradiate multiple respective regions on a sample, wherein the regions partially overlap one another along a first axis of the sample and are offset relative to one another along a second axis of the sample that is orthogonal to the first axis. The detector assembly is configured to detect the X-ray beams diffracted from the sample and to produce respective electrical signals in response to the detected X-ray beams. The scanning assembly is configured to move the sample relative to the source assembly and the detector assembly along the second axis. The processor is configured to identify defects in the sample by processing the electrical signals, which are produced by the detector assembly while the sample is moved.

In some embodiments, the apparatus includes respective slits that are located between the source assembly and the sample and are configured to form the multiple X-ray beams to have rectangular cross sections, such that the irradiated regions are rectangular. In other embodiments, the detector assembly includes an X-ray shield that is configured to prevent interference between detection of different X-ray beams. In yet other embodiments, the scanning assembly includes one or more clamps that are configured to support the sample mechanically during scanning, and the clamps include respective shields that are configured to block X-rays from being scattered from the clamps toward the detector assembly.

In an embodiment, the source assembly includes two or more X-ray sources. In another embodiment, the two or more X-ray sources are mounted in a staggered configuration, so as to produce the regions that partially overlap along the first axis of the sample and are offset relative to one another along the second axis of the sample. In yet another embodiment, the source assembly includes at least an X-ray source configured to produce an X-ray beam, and the apparatus further includes a beam splitter that is configured to split the X-ray beam into the multiple X-ray beams.

In some embodiments, the detector assembly includes two or more detectors that are mounted in a staggered configuration, so as to detect the X-ray beams diffracted from the regions that partially overlap along the first axis of the sample and are offset relative to one another along the second axis of the sample. In other embodiments, the detector assembly includes at least one detector, and the processor is configured to define on the at least one detector regions-of-interest corresponding to the X-ray beams diffracted from the respective regions on the sample.

There is additionally provided, in accordance with an embodiment of the present invention, a method for X-ray topography, including directing multiple X-ray beams, using a source assembly, so as to irradiate multiple respective regions on a sample, wherein the regions partially overlap one another along a first axis of the sample and are offset relative to one another along a second axis of the sample that is orthogonal to the first axis. The X-ray beams diffracted from the sample are detected by a detector assembly, and respective electrical signals are produced by the detector assembly in response to detecting the X-ray beams. The sample is moved, using a scanning assembly, relative to the source assembly and the detector assembly along the second axis. Defects in the sample are identified by processing the electrical signals, which are produced by the detector assembly while the sample is moved.

The present invention will be more fully understood from the following detailed description of the embodiments thereof, taken together with the drawings in which:

BRIEF DESCRIPTION OF THE DRAWINGS

FIG. 3 is a schematic illustration of an X-ray diffraction imaging (XRDI) system, in accordance with an embodiment of the present invention;

FIG. 4 is a schematic illustration of a scanning scheme of a wafer, in accordance with an embodiment of the present invention;

FIG. 5 is a schematic illustration of a detector assembly, in accordance with an embodiment of the present invention.

DETAILED DESCRIPTION OF EMBODIMENTS

Overview

Figure 1:
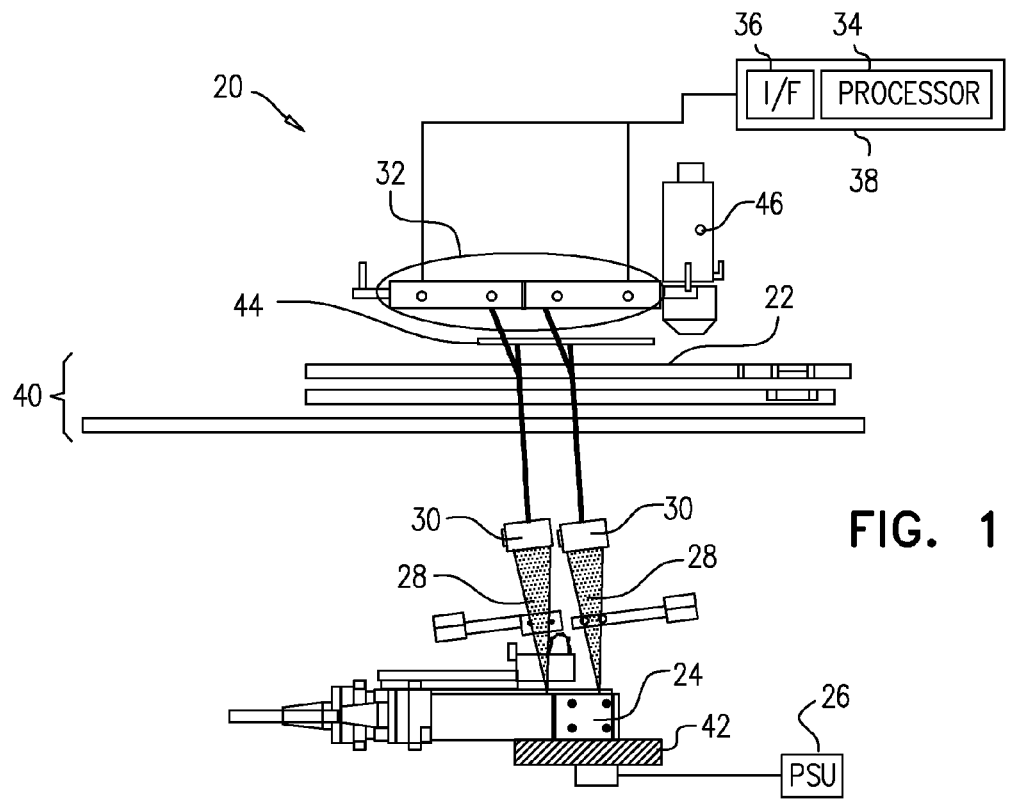
FIGS. 1 and 2 are schematic side views of an X-ray diffraction imaging (XRDI) system, in accordance with an embodiment of the present invention.

X-ray diffraction imaging (XRDI), also known as X-ray topography, may be used to detect defects in a crystalline wafer based on analyzing the intensity of the X-rays diffracted from the wafer. In a conventional XRDI system, an X-ray source directs a beam of X-rays to impinge on an area of one side of the wafer. An X-ray detector, which is positioned at an appropriate angle on the other side of the wafer, receives the X-rays that pass through the wafer and are diffracted from the irradiated area so as to form a diffraction image of the area. Typically, the source and detector are positioned symmetrically, at equal elevation angles with respect to the wafer that are chosen so that the detector receives the Laue diffraction from vertical crystal planes (substantially perpendicular to the surface of the wafer). Alternatively, other angular arrangements can be used to image Laue diffractions from other planes of the crystal. When the irradiated area is defect-free, the X-rays diffract uniformly from the desired crystal plane. Defects in the irradiated area typically appear as a changes in the diffracted intensity, either an increase or decrease as compared to the intensity from the defect-free crystal, due to distortions in the crystal planes in the area under test.

Such distortions are typically caused by defects of different types, such as (micro) cracks, dislocations, precipitates, and slip-bands that may be present in the bulk of the wafer. Optical inspection systems are typically configured to probe the surface of the sample, and are typically unable to detect and measure defects of this sort. XRDI techniques, on the other hand, provide high resolution imaging and more thorough check the bulk of the wafer. X-ray topography, however, has seen little adoption by the semiconductor industry for crystal defect inspection due to typical slow measurement and the large size of the apparatus required for measuring large wafers.

Embodiments of the present invention that are described herein provide improved methods and systems for high throughput measurements of X-ray topography using multiple X-ray beams. In the disclosed embodiments, an XRDI system inspects a large area of a moving sample (e.g., wafer) using multiple simultaneous X-ray beams. The system comprises a source assembly that irradiates the sample with the multiple X-ray beams, and a detector assembly that detects the diffracted beams.

In some embodiments, the source assembly may comprise a single X-ray source wherein the beam from the source is divided into multiple beams. In other embodiments, the source assembly may comprise multiple X-ray sources, each source producing one or more beams.

In the description that follows, the axis along which the sample is moved relative to the source and detector assemblies is referred to as the X-axis. The axis of the sample plane that is perpendicular to the X-axis is referred to as the Y-axis. In the disclosed embodiments, the source assembly is configured to direct the X-ray beams to impinge on different (e.g., adjacent) regions of the sample, wherein adjacent X-ray beams are positioned so that the irradiated regions are offset from one another along the X-axis, and overlap one another along the Y-axis.

In some embodiments, the detector assembly is positioned on the opposite side of the wafer relative to the source assembly, and is configured to detect the X-ray beams that are diffracted from the wafer, typically in a transmission geometry. In an embodiment, the assembly detector comprises a single detector. In other embodiments, the detector assembly may comprise multiple detectors that are typically arranged in a symmetrical configuration with respect to their corresponding sources.

In an embodiment, each beam passes through a respective slit located between the X-ray source assembly and the wafer, so as to generate a linear-shaped beam (e.g., a beam having a cross-section of a long and narrow rectangle) impinging on the wafer. A scanning assembly (e.g., a scanning stage) is configured to support the wafer and to move the wafer with respect to the X-ray source and detector assemblies, so as to scan the wafer with the linear X-ray beams, and thus, to generate a stripe of the X-rays to be detected by each of the corresponding detectors.

By applying this scanning scheme and configurations of source and detector assemblies, adjacent X-ray beams will typically cover overlapping stripes along the scanning direction using a staggered pattern arrangement of the detectors so as not to interfere with one another. In an embodiment, a processor is configured to receive electrical signals from the detectors, to analyze the signals so as to stitch the scanned stripes, and to generate a composite output image that is indicative of possible defects in the wafer.

In some cases, stray X-ray beams from an X-ray source may be scattered from materials comprised in the system and may interfere with signals of interest diffracted from the wafer. The use of multiple X-ray beams may increase the amount of such undesired X-ray radiation. In case of multiple detectors in the detector assembly, the detector assembly may comprise a shield, which is configured to pass each diffracted X-ray to the appropriate detector and to block stray scattered X-ray radiation.

Typically, the scanning stage comprises clamps that mechanically support the sample during scanning. In an embodiment, the clamps are shielded so as to block X-rays that may be scattered from the clamps toward the detectors.

The disclosed techniques provide high-throughput XRDI inspection using multiple X-ray beams that cover overlapping stripes, and at the same time eliminate cross-talk (i.e., unwanted scattering of X-rays into a detector from a source intended for another detector) between adjacent beams. The disclosed techniques may allow efficient scanning of the entire wafer, and thus may be used to improve the quality and reliability of semiconductor devices by detecting and possibly eliminating hidden defects, such as crystalline defects, from the bulk of the wafer.

System Description

FIG. 1 is a schematic side view of a system 20 for X-ray diffraction imaging (XRDI), in accordance with embodiments of the present invention. Aspects of system 20 are described in detail in the above-mentioned U.S. Pat. No. 8,781,070. System 20 is arranged to inspect a semiconductor wafer 22 (or any other suitable sample), for example in order to identify faults in a crystalline structure of the wafer, possibly created during fabrication, using methods described hereinbelow. The terms "sample" and "wafer" are used interchangeably in the present disclosure.

System 20 typically comprises a source assembly 24 that may comprise a single excitation source or multiple excitation sources, such as X-ray tubes 25A-25D (shown in FIG. 2), driven by one or more high-voltage power supply units (PSU) 26, for example one PSU 26 powers one tube (e.g., tube 25A), or any other suitable configuration as is known in the art. For example, four tubes 25A-25D may be used to illuminate an entire 300 mm wafer when the distance between assembly 24 and wafer 22 is less than 1 meter. When inspecting a 450 mm wafer, the number of tubes in assembly 24 may be increased, for example, to six.

In some embodiments, the type of tubes in assembly 24 may be a low-power microfocus type (less than 100 µm spot-size at a less than 100 W) or mid-power normal focus tubes (typically 1 mm spot-size at 2-3 kW). In other embodiments, assembly 24 may comprise one or more high-power microfocus tubes (typically 50-100 µm spot-size at 2-3 kW) such as a liquid metal jet tube, or any alternative suitable tube. Each tube in assembly 24 comprises an anode, which is typically made of molybdenum and operates at 50 kV to produce X-rays capable of penetrating wafer 22. Alternatively, other anode materials such as silver may also be used, depending on the application. Each tube in assembly 24 emits X-rays having a suitable energy range and power flux into X-ray optics (not shown). For each of the tubes, an associated motorized slit 30 is adjusted so as to shape beam 28 from the tube to have a cross-section of a long and narrow rectangle. Slit 30 is made of an X-ray opaque material. The position and size of slit 30 can be adjusted so as to adapt the X-ray beam divergence and spatial extent as appropriate.

In some embodiments, system 20 comprises a computer-controlled mechanical assembly, positioned between the tube and sample (not shown), for automatically switching a collimating crystal (not shown) in/out of the X-ray beam so as to increase the system resolution in certain applications. Passing beam 28 through the collimating crystal produces a substantially parallel and monochromatic beam, but reduces the intensity of the X-ray beam. The usage of the crystal can be switched on and off to allow switching between a high-intensity mode, and a low-noise mode without manual intervention. This capability allows the option for providing high-resolution rocking curves on the same system, which may be used by substrate manufacturers as a quality measure of the sample. The X-ray tubes, slits and optional crystal assemblies are mounted on a motorized rotation stage 42 (denoted source stage) with the axis of rotation centered at the wafer surface (not shown). Stage 42 is controlled by a processing unit 38, which may comprise a general-purpose computer that runs a suitable control software.

Stage 42 allows to adjust beam 28 to a desired angle with respect to the sample surface so as to inspect different diffraction planes of the crystal structure of wafer 22. In addition, stage 42 may be used for fine adjustment of an incidence angle in the vicinity of the selected diffraction plane prior to measurement, so as to compensate for local deformations of the wafer. When the collimating crystals are inserted between assembly 24 and wafer 22, stage 42 is configured to maintain the diffraction condition of the collimated beams in the event of wafer deformation, which causes a long-range change in the diffraction angle across the wafer.

In an embodiment, wafer 22 is mounted on a movable platform, such as an X-Y-$\phi$ stage 40, which enables moving the sample with respect to the X-ray beam in the X and Y directions, as well as applying azimuthal rotation $\phi$ about an axis perpendicular to the surface of the sample. Without loss of generality, the terms "X direction" and "X-axis" refer to the scan direction, i.e., the axis along which wafer 22 is scanned. The terms "Y direction" and "Y-axis" refer to the axis on the plane of the wafer that is orthogonal to the scan direction, as shown in detail in FIG. 3.

One of the linear axes (Y) may be reduced in range compared to the main scanning axis (X) or removed completely since the beam height spans a large fraction of the wafer diameter, or possibly the entire wafer or more. Moving stage 40 can be controlled by stepper motors, servo motors, or some combination thereof, which may be controlled, for example, by a processor running suitable motion-control software (not shown). The wafer may be moved along the X-axis in a series of small, discrete steps (step scanning) or at a constant speed (continuous scanning).

A detector assembly 32 is configured to detect the X-rays diffracted from wafer 22. A beam-stopper 44 made from an X-ray opaque material is located between wafer 22 and detector assembly 32, and is configured to occlude the directly transmitted beam from irradiating assembly 32. In addition, a first detector of assembly 32 (e.g., detector 33A shown in FIG. 3 below) should receive diffracted radiation solely from its corresponding first tube (e.g., tube 25A) of assembly 24. Beam-stopper 44 is configured to block undesired diffracted beams from irradiating detector 33A as a result of stray radiation from an adjacent second X-ray tube, such as tube 25B.

Detectors 33A-33D are arranged in a staggered pattern with overlapping regions between the individual detectors (as shown in FIGS. 3 and 5) so as cover the wafer without gaps. Each detector in assembly 32 is a two-dimensional (2D) position-sensitive X-ray camera that is adapted to measure the X-rays diffracted through wafer 22 according to Laue geometry, as a function of the detector position with respect to the surface of the wafer. In some embodiments, detector assembly 32 may comprise one or more charge-coupled device (CCD) or complimentary metal-oxide semi-conductor (CMOS) cameras featuring X-ray sensitive scintillator screens in the case of step scanning. In other embodiments, such as during continuous scanning, one or more time delay and integration (TDI) X-ray cameras, such as those manufactured by Hamamatsu Photonics (Japan) or by Teledyne DALSA (Waterloo, Ontario, Canada), may be used to increase signal-to-noise ratio (SNR) at high scanning speeds.

A review detector 46 is typically an x-ray sensitive CCD or a CMOS detector. Detector 46 is typically used for selected area imaging of crystalline defects at high-spatial resolution, e.g. 10 µm, that may have been located through the X-ray inspection at high throughput or from some external input, such as the coordinates supplied from an optical defect detection apparatus.

Additionally, the system may comprise an optical microscope (not shown) for visual inspection of surface defects or fiducials and for navigation on the wafer.

The irradiated region of the sample emits diffracted X-rays, which are captured by one of the detectors. Responsively to the captured X-rays, the detectors generate electrical signals, which are conveyed to signal processing unit 38. Unit 38 comprises a processor 34 (will be described in detail below), which is configured to process the electrical signals, and an interface 36 for communicating the electrical signals from detector assembly 32 to processor 34.

Processor 34 is configured to acquire data from the detectors and to determine a diffraction intensity image of the X-ray photons captured by the detectors. Processor 34 typically comprises a general-purpose computer, which performs these functions under the control of suitable software. The software is configured for detector control, data acquisition and data analysis, and may be downloaded to the processor in electronic form, over a network, for example, or it may alternatively be provided on tangible media, such as optical, magnetic or electronic memory media.

Figure 2:
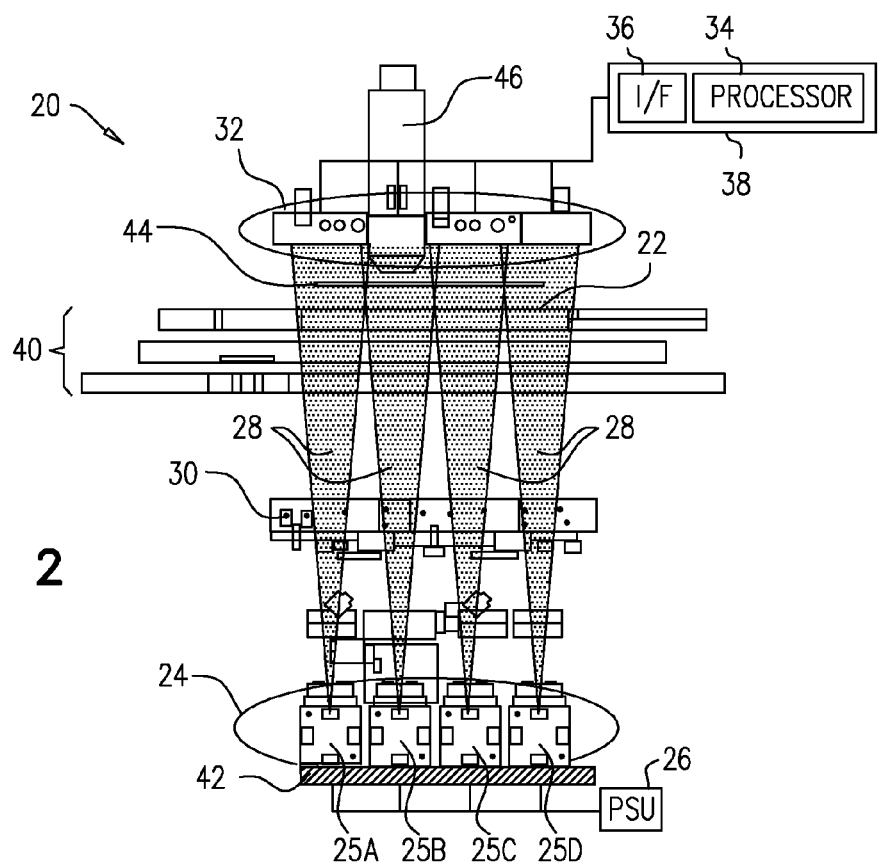

FIG. 2 is a schematic side view of system 20 for XRDI measurement, in accordance with embodiments of the present invention. The side view perspective of FIG. 2 is orthogonal to the side view perspective shown in FIG. 1.

Four tubes 25A-25D are arranged in a staggered pattern so as to produce X-ray beams that cover overlapping regions. For example, the four tubes may be arranged in two pairs with an offset between the pairs. Tubes 25A and 25C represent one pair, which is in front of the plane presented in FIG. 2, and tubes 25B and 25D represent the second pair, which is located on the rear of the FIG. 2 plane. This arrangement can be seen in three-dimensions in FIG. 3. Beams 28 are formed by slits 30 to have a rectangular cross-section. The long axis of the rectangular cross-section is shown in FIG. 2 and the short axis is shown in FIG. 1.

FIG. 3 is a schematic illustration of system 20 for XRDI measurement, in accordance with an embodiment of the present invention. FIG. 3 is a three-dimensional illustration of the system described in FIGS. 1 and 2 above. Four tubes 25A-25D are arranged with an offset in the X direction and are aligned in the Y direction. In some embodiments, the four corresponding detectors 33A-33D are arranged in a similar way, each detector facing its corresponding tube. In alternative embodiments, the detector assembly may comprise any suitable number of detectors that are able to detect all diffracted X-rays from wafer 22 and to eliminate cross-talk, such as a single detector that comprises virtual regions of interest defined by processor 34.

When stage 40 moves along wafer 22 in the X direction, the actual overlap between the regions irradiated by adjacent beams 28 occurs due to the staggered pattern arrangement of the detectors. This property is shown in FIG. 4. Wafer 22 is typically placed by a handling robot (not shown) on stage 40, which comprises three moving tables; for example a lower table for the X axis, a middle plate for the Y axis, and an upper plate for a rotation axis. All three plates are actually frames (no material in the center) so as to allow beam 28 to imping on the lower surface of wafer 22. The upper plate comprises clamps 48 so as to provide mechanical support to wafer 22 as will be described in FIG. 6.

Each X-ray tube 24 emits X-ray beam 28, which passes through wafer 22 and diffracted from a selected crystallographic plane under test (and thus, at a given angle related to the plane), from the upper surface of wafer 22, through beam-stopper 44, into the corresponding detectors.

FIG. 4 is a schematic illustration of a scanning scheme that can be used to scan wafer 22, in accordance with an embodiment of the present invention. As explained above, tubes 25A-25D are arranged in two pairs with an offset in the X direction and with an overlap in the Y direction. Tubes 25A-25D emit respective X-ray beams that are shaped by slits 30 and thus irradiate rectangular regions 31A-31D on the wafer surface. The four X-ray beams are diffracted from wafer 22 towards respective detectors in assembly 32.

This configuration allows an overlap during scanning, but ensures that radiation from a given point on wafer 22 at a given time is detected only by the appropriate detector. In other words, adjacent detectors do not collect XRDI signals from the same point on the wafer at the same time. For example, when the wafer is scanned along the X-axis, irradiated regions 31A and 31B form diffraction stripes 27A and 27B, respectively. An overlap area 29 is comprised in both stripes 27A and 27B and thus, scanned twice, but at different times, first by region 31B and later by region 31A.

This offset in time and space is managed, for example, by a software program, which is configured to construct the image based on the location in space of the diffraction stripe for each combination of tube and its respective detector. In an embodiment, this image construction can be done after completing the measurement over the entire wafer. In another embodiment, the image from each camera can be constructed as each stripe is collected by the camera using "on-the-fly stitching" techniques. Using this approach, the whole wafer may be imaged with a single sweep across the wafer.

Scattered X-Rays and Interference Between X-Ray Tubes and Detectors

FIG. 5 is a schematic illustration of detector assembly 32, in accordance with an embodiment of the present invention. Four detectors 33A-33D are arranged in two pairs with offset in the X direction and with overlap in the Y direction. One of the pairs comprises detectors 33A and 33C and the other pair comprises detectors 33B and 33D. During wafer scanning, the beams are diffracted from wafer 22 toward their respective detectors so as to form diffraction stripes. The detector output signals are processed by the software running on processor 34, which constructs an image from all or some of the stripes. For example, tube 25A creates region 31A, which is shaped by slit 30 and impinges on wafer 22. Detector 33B receives region 31B as diffracted from wafer 22 and processor 34 creates stripe 27B. The same flow is conducted at all tubes and detectors and all the output stripes (and thus overlaps, such as overlap 29) are processed by processor so as to create an image, which indicates possible defects on wafer 22.

The X-ray beams are typically polychromatic, and thus may diffract from the illuminated portion of wafer 22 in any direction. A diffracted beam that is addressed to a given detector may be also detected by adjacent detectors as interference that may cause image degradation, including additional "nuisance lines" and intensity variations. In addition, interaction between the beam and the various elements of system 20 may create scattered X-ray radiation that may interfere with signals of interest scattered from the wafer. The use of multiple X-ray tubes may increase the amount of undesired X-ray radiation emitted from adjacent tubes or scattered from elements of system 20. Means for protecting from such cross-talk are described herein.

In some embodiments, shields 43, 45 and 47 are attached to detector assembly 32 so as to block cross-talk radiation originated from interfering sources. The shields are typically made from an X-ray opaque material. For example, shield 45 is located between detectors 33A and 33C so as to block cross talk between tube 25A and detector 33C, and between tube 25C and detector 33A. Shield 43 is located between the two pairs of detectors so as to block cross-talk radiation, for example, between tube 25D and detector 33C. Likewise, shield 47 blocks, for example, possible cross-talk between tube 25B and detector 33D.

Figure 6:
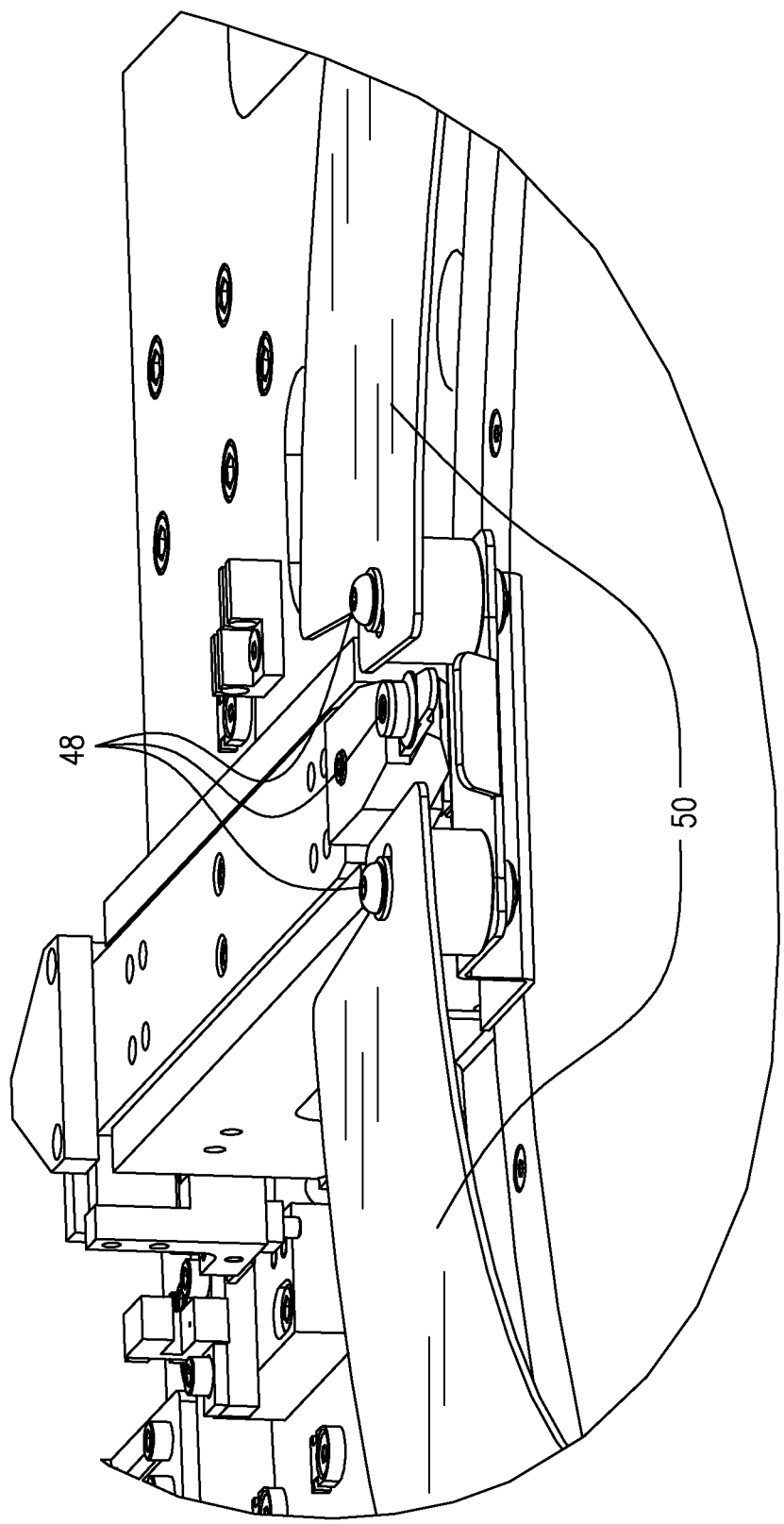
FIG. 6 is a schematic illustration of sample clamps with shielding, in accordance with an embodiment of the present invention.

FIG. 6 is a schematic illustration of clamping accessories for positioning wafer 22, in accordance with an embodiment of the present invention. During the measurement process, in order to accurately detecting defects and their locations, wafer 22 must be kept at an accurate position with respect to assemblies 24 and 32. The upper plate of stage 40 typically comprises clamps 48, which are configured to hold wafer 22 stationary on stage 40 while the stage moves during scanning.

When wafer 22 is measured in a transmission geometry by multiple beams, one or more the beams may interact with the materials that comprise clamps 48. The clamps may scatter stray X-ray radiation that may interfere with signals of interest that are scattered from the wafer, and thus, may degrade the measurement quality.

In some embodiments, a labyrinth arrangement of shielding 50 made from an X-ray opaque material is provided around clamps 48 so as to allow exposure of the entire wafer to the incident X-ray radiation, and yet, to prevent scattering from the supporting clamps to appear within the image. In other embodiments, the clamps may comprise an X-ray opaque material, and in yet other embodiments, the mechanical shape and size of the clamps may be chosen to substantially reduce the X-ray radiation scattered from the clamps.

The examples of FIGS. 1-6 refer to a specific configuration of X-ray system 20. This configuration, however, is chosen purely for the sake of conceptual clarity. In alternative embodiments, the disclosed techniques can be used, mutatis mutandis, in various other types of XRDI systems or analyzing modules, comprising any suitable excitation source, power supplies, focusing optics and detection system. For example, the source assembly may comprise a single source that emits a single X-ray beam into a beam splitter that splits the beam into multiple X-ray beams. In case of multiple sources and multiple detectors, the number of sources and detectors may be different. Moreover, a single source may be associated with multiple detectors, and a single detector may be associated with multiple sources.

It will be appreciated that the embodiments described above are cited by way of example, and that the following claims are not limited to what has been particularly shown and described hereinabove. Rather, the scope includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for overlapped X-ray diffraction imaging, comprising:
    a source assembly, which comprises multiple X-ray sources that, for a predefined direction of scanning, (i) partially overlap one another along an axis orthogonal to the direction of scanning and (ii) are offset relative to one another along the direction of scanning, wherein the X-ray sources are configured to direct multiple respective X-ray beams so as to irradiate, on a first surface of a sample, multiple respective regions that (i) partially overlap one another along the axis orthogonal to the direction of scanning and (ii) are offset relative to one another along the direction of scanning;
    a detector assembly, which comprises multiple X-ray detectors that (i) partially overlap one another along the axis orthogonal to the direction of scanning and (ii) are offset relative to one another along the direction of scanning, wherein the X-ray detectors are configured to detect the respective X-ray beams that are directed by the X-ray sources, enter the sample at the first surface, are diffracted while passing through the sample and exit the sample at a second surface that is opposite to the first surface, and to produce respective electrical signals in response to the detected X-ray beams;
    a scanning assembly, which is configured to move the sample relative to the source assembly and the detector assembly along the direction of scanning; and
    a processor, which is configured to identify defects in the sample by creating a diffracted X-ray intensity image from the electrical signals, which are produced by the detector assembly while the sample is moved, and detecting in the diffracted X-ray intensity image changes relative to a defect-free crystal.

2. The apparatus according to claim 1, and comprising respective slits that are located between the source assembly and the sample and are configured to form the multiple X-ray beams to have rectangular cross sections, such that the irradiated regions are rectangular.

3. The apparatus according to claim 1, wherein the detector assembly comprises an X-ray shield that is configured to prevent interference between detection of different X-ray beams.

4. The apparatus according to claim 1, wherein the scanning assembly comprises one or more clamps that are configured to support the sample mechanically during scanning, and wherein the clamps comprise respective shields that are configured to block X-rays from being scattered from the clamps toward the detector assembly.

5. The apparatus according to claim 1, wherein the X-ray sources are mounted in a staggered configuration, so as to produce the regions that partially overlap along the axis orthogonal to the direction of scanning and are offset relative to one another along the direction of scanning.

6. The apparatus according to claim 1, wherein the X-ray detectors are mounted in a staggered configuration, so as to detect the X-ray beams diffracted from the regions that partially overlap along the axis orthogonal to the direction of scanning and are offset relative to one another along the direction of scanning.

7. The apparatus according to claim 1, wherein the processor is configured to define on at least one of the X-ray detectors one or more regions-of-interest corresponding to the X-ray beams diffracted from the respective regions on the sample.

8. A method for overlapped X-ray diffraction imaging, comprising:
    directing multiple X-ray beams, using a source assembly which comprises multiple X-ray sources that, for a predefined direction of scanning, (i) partially overlap one another along an axis orthogonal to the direction of scanning and (ii) are offset relative to one another along the direction of scanning, so as to irradiate multiple respective X-ray beams on multiple respective regions of a first surface of a sample that (i) partially overlap one another along the axis orthogonal to the direction of scanning and (ii) are offset relative to one another along the direction of scanning;

using a detector assembly which comprises multiple X-ray detectors that (i) partially overlap one another along the axis orthogonal to the direction of scanning and (ii) are offset relative to one another along the direction of scanning, detecting the respective X-ray beams that are directed by the X-ray sources, enter the sample at the first surface, are diffracted while passing through the sample and exit the sample at a second surface that is opposite to the first surface, and producing, by the detector assembly, respective electrical signals in response to detecting the X-ray beams;

moving the sample, using a scanning assembly, relative to the source assembly and the detector assembly along the direction of scanning; and identifying defects in the sample by creating a diffracted X-ray intensity image from the electrical signals, which are produced by the detector assembly while the sample is moved, and detecting in the diffracted X-ray intensity image changes relative to a defect-free crystal.

9. The method according to claim 8, wherein directing the multiple X-ray beams comprises forming the multiple X-ray beams to have rectangular cross sections by passing the X-ray beams through respective slits that are located between the source assembly and the sample so as to, such that the irradiated regions are rectangular.

10. The method according to claim 8, wherein detecting the X-ray beams comprises preventing interference between detection of different X-ray beams using an X-ray shield.

11. The method according to claim 8, wherein moving the sample comprises supporting the sample mechanically during scanning using clamps, and comprising blocking X-rays from being scattered from the clamps toward the detector assembly using respective shields applied to the clamps.

12. The method according to claim 8, wherein directing the X-ray beams comprises mounting the X-ray sources in the source assembly in a staggered configuration, so as to produce the regions that partially overlap along the axis orthogonal to the direction of scanning and are offset relative to one another along the direction of scanning.

13. The method according to claim 8, wherein detecting the X-ray beams comprises mounting the X-ray detectors on the detector assembly in a staggered configuration, so as to detect the X-ray beams diffracted from the regions that partially overlap along the axis orthogonal to the direction of scanning and are offset relative to one another along the direction of scanning.

14. The method according to claim 8, wherein detecting the X-ray beams comprises defining on at least one of the X-ray detectors one or more regions-of-interest corresponding to the X-ray beams diffracted from the respective regions on the sample.

* * * * *